(12) United States Patent
Hendricks et al.

(10) Patent No.: US 10,731,041 B2
(45) Date of Patent: Aug. 4, 2020

(54) CONDUCTIVE POLYMER COATINGS FOR THREE DIMENSIONAL SUBSTRATES

(71) Applicant: Heraeus Medical Components LLC, St. Paul, MN (US)

(72) Inventors: Jeffrey Hendricks, Ann Arbor, MI (US); Kyle Mallires, Ann Arbor, MI (US); Sarah Richardson-Burns, Ann Arbor, MI (US)

(73) Assignee: HERAEUS MEDICAL COMPONENTS LLC, St. Paul, MN (US)

( * ) Notice: Subject to any disclaimer, the term of this patent is extended or adjusted under 35 U.S.C. 154(b) by 1132 days.

(21) Appl. No.: 14/944,735

(22) Filed: Nov. 18, 2015

(65) Prior Publication Data

US 2016/0177109 A1 Jun. 23, 2016

Related U.S. Application Data

(60) Provisional application No. 62/081,986, filed on Nov. 19, 2014.

(51) Int. Cl.

| | |
|---|---|
| *C09D 5/24* | (2006.01) |
| *D06M 15/356* | (2006.01) |
| *A61L 29/14* | (2006.01) |
| *C04B 41/48* | (2006.01) |
| *A61L 29/08* | (2006.01) |
| *C09D 145/00* | (2006.01) |
| *H01M 4/60* | (2006.01) |
| *C08L 101/12* | (2006.01) |
| *A61N 1/04* | (2006.01) |
| *H01M 4/00* | (2006.01) |
| *C09D 201/00* | (2006.01) |
| *C09D 165/00* | (2006.01) |
| *H01M 4/36* | (2006.01) |
| *C08J 7/04* | (2020.01) |
| *C04B 41/83* | (2006.01) |
| *D06M 101/40* | (2006.01) |

(52) U.S. Cl.
CPC ............. *C09D 5/24* (2013.01); *A61L 29/085* (2013.01); *A61L 29/14* (2013.01); *A61N 1/04* (2013.01); *C04B 41/4849* (2013.01); *C04B 41/83* (2013.01); *C08J 7/0427* (2020.01); *C08L 101/12* (2013.01); *C09D 145/00* (2013.01); *C09D 165/00* (2013.01); *C09D 201/00* (2013.01); *D06M 15/3566* (2013.01); *H01M 4/00* (2013.01); *H01M 4/366* (2013.01); *H01M 4/608* (2013.01); *A61L 2420/02* (2013.01); *A61L 2420/06* (2013.01); *C08G 2261/1424* (2013.01); *C08G 2261/3223* (2013.01); *C08G 2261/512* (2013.01); *C08G 2261/794* (2013.01); *C08J 2375/04* (2013.01); *C08J 2400/12* (2013.01); *C08J 2465/00* (2013.01); *D06M 2101/40* (2013.01)

(58) Field of Classification Search
USPC ....... 428/336, 209, 220, 327, 419, 447, 141, 428/148, 172, 195.1, 208, 213, 216, 323, 428/329, 331, 337, 36.91, 372, 402, 412, 428/413, 422, 446, 523, 689, 696, 704; 427/58, 79, 126.1, 80, 108, 122, 126.3, 427/301, 327, 379, 397.7, 488, 517, 535, 427/553, 555, 96.1, 97.1, 98.4, 99.2; 252/500, 514, 512, 502, 511, 513, 478, 252/503, 510, 518.1, 519.31, 519.33, 252/519.34, 520.1, 521.3
See application file for complete search history.

(56) References Cited

U.S. PATENT DOCUMENTS

| | | | |
|---|---|---|---|
| 6,132,752 A | 10/2000 | Pickett et al. | |
| 7,013,182 B1 * | 3/2006 | Krishnan | A61N 1/0563 607/119 |
| 7,708,908 B2 | 5/2010 | Kim et al. | |
| 8,005,526 B2 | 8/2011 | Martin et al. | |
| 8,343,212 B2 | 1/2013 | Pickett et al. | |
| 8,380,306 B2 | 2/2013 | Pickett | |
| 8,577,476 B2 | 11/2013 | Hendricks et al. | |
| 8,936,794 B2 | 1/2015 | Martin et al. | |
| 9,050,454 B2 | 6/2015 | Hendricks et al. | |
| 9,084,546 B2 | 7/2015 | Richardson-Burns et al. | |
| 2003/0062510 A1 | 4/2003 | Van den Bogaert | |
| 2007/0278453 A1 | 12/2007 | Zahn et al. | |
| 2010/0252782 A1 * | 10/2010 | Masahiro | C09D 5/24 252/511 |

(Continued)

FOREIGN PATENT DOCUMENTS

| | | |
|---|---|---|
| CN | 101081896 | 12/2007 |
| CN | 102333825 | 1/2012 |

(Continued)

OTHER PUBLICATIONS

Sessolo, M., et al., "Easy-to-Fabricate Conducting Polymer Microelectrode Arrays," 2013, Adv Mater, 1-5, wileyonlinelibrary.com.

English translation of First Office Action and Search Report dated Feb. 2, 2019 for counterpart Chinese Patent Application No. 2015800696519 by the Chinese State Intellectual Property Office (now known as China National Intellectual Property Administration).

English translation of Notice of Reasons for Refusal dated Nov. 9, 2018 and Record of Result of Prior Art Search received from the Japanese Patent Office for counterpart Japanese Patent Application No. 2017-527815.

English translation of Official action dated May 7, 2019 received from the Korean Intellectual Property Office for counterpart Korean Patent Application No. 10-2017-7016673.

*Primary Examiner* — Aaron Austin
*Assistant Examiner* — Kevin C Ortman, Jr.
(74) *Attorney, Agent, or Firm* — Stradley Ronon Stevens & Young LLP

(57) ABSTRACT

The present invention generally relates to compositions and methods for the preparation of conductive polymer coatings, and methods for application of the coatings to three-dimensional substrates.

16 Claims, No Drawings

(56) References Cited

U.S. PATENT DOCUMENTS

| | | |
|---|---|---|
| 2010/0312331 A1 | 12/2010 | Pickett et al. |
| 2011/0175036 A1* | 7/2011 | Masahiro ................. C08J 7/047 252/500 |
| 2011/0248223 A1 | 10/2011 | Zheng |
| 2011/0257504 A1 | 10/2011 | Hendricks et al. |
| 2011/0310053 A1 | 12/2011 | Kim et al. |
| 2012/0147528 A1* | 6/2012 | Biler ...................... H01G 9/025 361/525 |
| 2013/0284982 A1* | 10/2013 | Chen ........................ C09D 5/24 252/478 |
| 2014/0227318 A1 | 8/2014 | Urade et al. |
| 2014/0277318 A1 | 9/2014 | Richardson-Burns et al. |
| 2015/0303477 A1 | 10/2015 | Lövenich et al. |
| 2016/0086685 A1 | 3/2016 | Mallires et al. |

FOREIGN PATENT DOCUMENTS

| | | |
|---|---|---|
| CN | 104946124 | 9/2015 |
| JP | 2004532307 | 10/2004 |
| JP | 2008-098104 | 4/2008 |
| JP | 2010-077187 | 4/2010 |
| JP | 2010-106245 A | 5/2010 |
| JP | 2012-004092 | 1/2012 |
| JP | 2012-097132 A | 5/2012 |
| JP | 2013-216766 | 10/2013 |
| TW | 201012884 A | 4/2010 |
| WO | 2014154360 A3 | 10/2014 |
| WO | 2015031265 A1 | 3/2015 |

* cited by examiner

CONDUCTIVE POLYMER COATINGS FOR THREE DIMENSIONAL SUBSTRATES

CROSS-REFERENCE TO RELATED APPLICATIONS

This application claims the benefit of U.S. Provisional Patent Application Ser. No. 62/081,986, filed Nov. 19, 2014, the entirety of which is herein incorporated by reference.

FIELD OF THE INVENTION

The present invention generally relates to compositions and methods for the preparation of conductive polymer coatings, and methods for application of the coatings to three-dimensional substrates.

BACKGROUND OF THE INVENTION

A variety of devices on the market today utilize electrode coatings comprised of metal oxides or metal nitrides. Depending on how they are deposited, coatings comprised of metal oxides or metal nitrides can have a variety of topographies and morphologies. Traditional metal oxide electrodes, however, are mechanically hard and are sensitive to the build-up of brittle oxide layers at the surface of the electrode. These properties make metal oxide electrodes undesirable for use in applications where flexibility and/or biological compatibility are required.

Conductive polymer coatings have the potential to overcome some of the drawbacks associated with traditional metal oxide or metal nitride coatings. For example, conductive polymer coatings derived from poly(3,4-ethylenedioxythiophene) (PEDOT) have been widely used in the electronics industry. The conductive polymer coatings known in the art, however, have primarily been formulated for application as thin films over flat, two-dimensional substrate surfaces.

It is desirable to develop a conductive coating that provides excellent electrical conductivity, and is biologically acceptable for use in medical device applications, and exhibits greater mechanical, chemical, and electrical stability than the coatings known in the art, such that it is suitable for conformal application to three-dimensional substrate surfaces.

In addition, the conductive polymer coatings known in the art have primarily been applied to rigid, inflexible surfaces. The coatings known in the art often lack flexibility and/or crack resistance, and will often exhibit a loss of conductivity after being subjected to repeated flexing cycles. It is therefore desirable to develop a conductive coating that is mechanically and electrically durable for application to substrate surfaces having a high degree of flexibility.

DESCRIPTION OF THE INVENTION

It has been discovered electrically conductive polymeric coatings can be prepared that are suitable for application to three-dimensional substrates and/or to substrate surfaces having a high degree of flexibility.

As used herein, the term "three-dimensional substrate" means a substrate comprising a surface that is convex, concave, or angular (i.e., a surface that is not substantially flat).

The coatings described herein address a number of drawbacks exhibited by existing state of the art, and provide superior conductivity, durability, and abrasion resistance. Most significantly, the coatings provide superior adhesion to substrate surfaces and allow for conformal application to three-dimensional substrates. The coatings described herein also provide improved mechanical properties that allow for application to flexible substrates.

Coating Precursor Composition

One aspect of the present invention is directed to a coating precursor composition that is adapted for use in applying conformal coatings to three-dimensional substrates. The coating precursor composition may comprise one or more of the components described below.

Conductive Polymer

The coating precursor composition comprises a conductive polymer.

Generally, conductive polymers comprise multiple conductive repeat units assembled into chains with conjugated alternating single and double carbon-carbon bonds. Conductive polymers are also sometimes referred to as inherently or intrinsically conductive polymers, electroactive polymers, or conjugated polymers. Conductive polymers are ideally suited for joining or interfacing electronic and ionic systems, because they are capable of conductive both electronic and ionic charge. Conductive polymers can also utilize highly effective and efficient charge storage and transfer mechanisms, similar to capacitors. Without being bound to a particular theory, it is believed that conductive polymers facilitate efficient charge transport through delocalized electrons across conjugated alternating double-single carbon-carbon bonds along the molecular backbone.

Typically, the conductive polymer is cationic. For example, the conductive polymer typically carries an average charge per repeat unit of from about +0.1 to about +1.0. More typically, the conductive polymer carries an average charge per repeat unit of from about +0.25 to about +0.5, and most typically an average charge per repeat unit of about +0.33.

The conductive polymer can comprise a polyacetylene, a poly(fluorene), a polyphenylene, a polyphenylene vinylene, a polypyrene, a polyazulene, a polynaphthalene, a poly (pyrrole), a polycarbazole, a polyindole, a polyazepine, a polyaniline, a polyacene, a polythiophene, a polythiophene vinylene, a poly(p-phenylene sulfide), a polypyridine, or functionalized derivatives, precursors or blends thereof.

Usually, the conductive polymer comprises poly(3,4-ethylenedioxythiophene), or a functionalized derivative thereof. For example, the conductive polymer can be derived from 3,4-ethylenedioxythiophene.

Alternatively, the conductive polymer can be derived from a functionalized derivative of 3,4-ethylenedioxythiophene (EDOT) comprising hydroxymethyl-EDOT, EDOT-vinyl, EDOT-ether allyl, EDOT-COOH, EDOT-MeOH, EDOT-silane, EDOT-vinyl, EDOT-acrylate, EDOT-sulfonate, EDOT-amine, or EDOT-amide. More typically, the functionalized derivative of 3,4-ethylenedioxythiophene (EDOT) comprises hydroxymethyl-EDOT, EDOT-vinyl, EDOT-ether allyl, or EDOT-acrylate.

The conductive polymer can comprise poly(hexylthiophene), or a salt or functionalized derivative thereof. The conductive polymer can comprise poly-4-vinylpyridine. The conductive polymer can comprise poly(diallyldimethylammonium chloride).

The conductive polymer is typically provided to the coating precursor composition in the form of a dispersion. For example, the conductive polymer may be provided as an aqueous dispersion.

Primary Counterion

The coating precursor composition usually comprises a primary counterion component that substantially neutralizes the charged functional groups associated with the conductive polymer, and further can provide the resulting polymeric coating with improved electrical, chemical, and mechanical properties as desired for a particular application.

Generally, the primary counterion comprises one or more repeat units having a negatively charged functional group.

For example, the negatively charged functional group can be a phosphate group, a phosphonate group, a sulfamate group, a carboxylate group, a sulfate group, a sulfonate group, or a combination thereof.

Further, the negatively charged functional group can comprise a phosphate group, a carboxylate group, a sulfate group, a sulfonate group, or a combination thereof. Typically, the negatively charged functional group comprises a sulfonate group, a carboxylate group, or a combination thereof. More typically, the negatively charged functional group comprises a sulfonate group.

The negatively charged functional group can comprise a counterion. The counterion can be a proton, an ammonium ion, an organic cation, an alkali metal cation, or an alkaline earth metal cation. For example, the counterion can be sodium, potassium, calcium, magnesium, ammonium, or a combination thereof.

The sulfonate group can comprise a counterion. For example, the sulfonate group can comprise a sodium counterion.

By way of non-limiting example, the primary counterion component may comprise polyvinyl sulfonate, polystyrene sulfonate, polyallyl sulfonate, polyethyl acrylate sulfonate, polybutyl acrylate sulfonate, polyacryl sulfonate, polymethacryl sulfonate, poly-2-acrylamide-2-methylpropane sulfonate, polyisoprene sulfonate, polyvinyl carboxylate, polystyrene carboxylate, polyallyl carboxylate, polyacryl carboxylate, polymethacryl carboxylate, poly-2-acrylamide-2-methylpropane carboxylate, polyisoprene carboxylate, polyacrylates, polyamino acids (e.g., polyglutamates), polydopamine, sulfonated poly ether ether ketone (S-PEEK), sulfonated polyurethanes (polyurethane ionomers), or a combination thereof.

As a further non-limiting example, the primary counterion component may comprise sulfonic acid, fluorosulfonate, toluene sulfonate, taurine, anthraquinone sulfonate, vinyl sulfonate, 2-acrylamido-2-methyl-1-propanesulfonic acid, polystyrene sulfonate, polyvinyl sulfonate, sulfonated polytetrafluoroethylene, polyanetholesulfonic acid, a salt or functionalized derivative thereof, or a combination thereof.

Also, the primary counterion component can comprise paratoluene sulfonate (pTS), 4-vinylbenzenesulfonate, vinyl sulfonate, a polymer thereof, or a combination thereof. The primary counterion component can comprise sulfonated polytetrafluoroethylene (sold under the trade name NAFION).

The primary counterion component can comprise a block copolymer derived from polystyrene sulfonate and maleic anhydride (PSS-CoMA). Further, the primary counterion component can comprise a mixture of polystyrene sulfonate and PSS-CoMA.

The primary counterion component can comprise a primary copolymer, a primary block copolymer, a primary multi-block copolymer, or a combination thereof wherein one or more of the repeat units or blocks are functionalized with a negatively charged functional group. The negatively charged functional group can be selected as described in detail above.

For example, the primary counterion component can comprise a copolymer or block-copolymer comprising sulfonated polystyrene-ethylene, sulfonated polystyrene-butadiene, sulfonated polystyrene-isoprene, or a combination thereof.

The primary counterion component can comprise a random copolymer comprising a negatively charged functional group. The negatively charged functional group can be selected as described in detail above.

Usually, the random copolymer comprises (a) styrenic repeat units comprised of styrene, t-butyl styrene, methyl styrene, a carboxylic acid-functionalized styrene (e.g., vinyl benzoic acid), an amine-functionalized styrene (e.g., diethylamino ethylstyrene), or combinations thereof, and (b) elastomeric repeat units comprised of polyethylene, polybutylene, polybutadiene, polyisoprene, polyisobutylene, or combinations thereof, wherein from about 10 to 100 mole percent of the repeat units are functionalized with a negatively charged functional group. The negatively charged functional group can be selected as described in detail above.

For example, the primary counterion component can comprise sulfonated polystyrene-r-ethylene (SPSE).

Generally, the primary counterion component can comprise a mixture of two or more species of polystyrene sulfonate having different molecular weights.

The primary counterion component can comprise polystyrene sulfonate (PSS), sulfonated polystyrene-block-poly(ethylene-r-butylene)-block-polystyrene (SPSEBS), polystyrene-block-polyisobutylene-block-polystyrene (SPSIBS), sulfonated polystyrene-r-ethylene (SPSE), a block copolymer derived from polystyrene sulfonate and maleic anhydride (PSS-CoMA), sulfonated polytetrafluoroethylene (sold under the trade name NAFION), polyanetholesulfonic acid, sulfonated poly ether ether ketone (S-PEEK), sulfonated polyurethanes (polyurethane ionomers), poly(2-acrylamido-2-methyl-1-propanesulfonic acid), polyvinyl sulfonate, sulfonated polytetrafluoroethylene, a salt or functionalized derivative thereof, or a combination thereof.

The primary counterion component can comprise carbon nanotubes functionalized with a negatively charged functional group which can be selected as described in detail above.

The primary counterion component can comprise carbon nanotubes functionalized with polyaminobenzene sulfonate.

The primary counterion component can comprise functionalized carbon nanotubes in combination with one or more additional primary species as described above. Typically, the one or more additional primary species comprise polystyrene sulfonate (PSS), sulfonated polystyrene-block-poly(ethylene-r-butylene)-block-polystyrene (SPSEBS), polystyrene-block-polyisobutylene-block-polystyrene (SPSIBS), sulfonated polystyrene-r-ethylene (SPSE), a block copolymer derived from polystyrene sulfonate and maleic anhydride (PSS-CoMA), sulfonated polytetrafluoroethylene, salts and functionalized derivatives thereof, or combinations thereof.

Preferably, the primary counterion comprises polystyrene sulfonate (PSS).

PEDOT:PSS Aqueous Dispersions

The conductive polymer can comprise poly(3,4-ethylenedioxythiophene) (PEDOT) and the primary counterion can comprise PSS. Aqueous dispersions of PEDOT and PEDOT:PSS are commercially available from a number of suppliers and are preferred for use in the methods, coatings, and precursor compositions described herein.

Dispersions of the conductive polymer having high conductivity are preferred. For example, CLEVIOS PH 1000 is a high-conductivity grade PEDOT:PSS dispersion that is particularly preferred.

Solvents

The coating precursor composition further comprises one or more solvents.

A solvent may be added to the precursor composition to adjust the viscosity, surface tension, pH, or volatility of the composition, or to dilute the composition to reduce the concentration of the conductive polymer.

The precursor composition typically comprises water. As noted above, the conductive polymer is typically provided to the precursor composition in the form of an aqueous dispersion. Additional water may be added to further dilute the composition.

The precursor composition may also comprise one or more organic solvents. Non-limiting examples of organic solvents include methanol, ethanol, isopropyl alcohol, 1-propanol, 1-butanol, acetone, methyl ethyl ketone, dimethyl sulfoxide, dimethylformamide, propylene carbonate, tetrahydrofuran, acetic acid, diethyl ether, and ethyl acetate.

Secondary Doping Agents

The coating precursor composition may further comprise one or more secondary doping agents that improve the conductivity of the coating.

Non-limiting examples of secondary doping agents include low volatility polar solvents such as ethylene glycol, sorbitol, glycerol, dimethylsulfoxide, N,N-dimethylformamide, erythritol, 2-nitroethanol, methoxyphenol, N,N-dimethylacetamide, N-methylpyrrolidone, succinimide, and propylene glycol.

The secondary doping agent may comprise ethylene glycol, propylene glycol, dimethylsulfoxide, glycerol, or sorbitol.

Ethylene glycol is a preferred secondary doping agent. Because ethylene glycol has a relatively low boiling point compared to other doping agents, the curing process can be carried out at a relatively low temperature. The use of a low temperature curing step is beneficial in that it allows for the use of a wider range of substrates, and is particularly beneficial when the coatings are applied to polymer substrates.

In most cases, the secondary doping agent is mostly or completely removed from the coating composition during the thermal curing step. In some cases, however, it is desirable to use a secondary doping agent that is non-toxic. Propylene glycol and dimethyl sulfoxide are preferred species where a non-toxic doping agent is desirable.

The secondary doping agent is typically included in a concentration of from about 1% to about 40% of the composition on a weight per volume basis. More typically, the concentration of the secondary doping agent is from about 2% to about 30% w/v, and more typically from about 4% to about 25% w/v.

Surfactants

The coating precursor composition may further comprise one or more surfactants.

By modifying the surface tension of the precursor composition, surfactants can be used to improve wettability and to promote uniform application of the composition onto the substrate during the dip coating process, resulting in a more uniform coating on the final product.

Surfactants can also be introduced to solubilize and/or stabilize the components in the precursor composition. In general, and although there are some exceptions to this rule, the conductive polymers described herein tend to be hydrophobic, while the primary counterions and secondary doping agents described herein tend to be hydrophilic. Surfactants can be employed to create an emulsion or colloidal suspension where, even with very different levels of hydrophobicity/hydrophilicity, multiple reagents can be effectively held in a partially solvated state through interaction with the amphiphilic surfactant molecules.

Preferably, the surfactant component also enhances the conductivity of the coating.

Non-limiting examples of suitable anionic surfactants include alkylsulfonic acids and alkylbenzenesulfonic acids and salts thereof (e.g., dodecylbenzenesulfonic acid, octylbenzenesulfonic acid), organosulfates and salts thereof (e.g., sodium dodecyl sulfate), carboxylates and natural fatty acids, and salts thereof (e.g., sodium stearate, oleic acid).

Non-limiting examples of suitable nonionic surfactants include poloxamers and block copolymers (e.g., PLURONICS series surfactants), fatty alcohols (e.g., 1-octanol, 1-dodecanol), ethoxylated fatty alcohols, alkylphenol ethoxylates, polyoxyethylene glycol alkyl ethers (e.g., BRIJ compositions, TRITON X-100), glycerol alkyl esters (e.g., glycerol laurate), polyoxyethylene glycol sorbitan alkyl esters (e.g., polysorbate), and silicone-based surfactants (e.g., silicone polyoxyalkylene copolymer).

Dodecylbenzenesulfonic acid (DBSA) is a preferred anionic surfactant. Without being bound to a particular theory, it is believed that DBSA acts enhances the conductivity of compositions comprising PEDOT:PSS as a conductive polymer. Sodium dodecyl sulfate is structurally similar to DBSA, and is also a preferred anionic surfactant.

Preferred nonionic surfactants include poloxamers and block copolymers (e.g., PLURONICS series surfactants).

The surfactant component is typically included in a concentration of from about 0.01% to about 5% of the precursor composition on a weight per volume basis. More typically, the concentration of the surfactant component is from about 0.1% to about 1% w/v, and more typically from about 0.2% to about 0.5% w/v.

Crosslinking Agents

The coating precursor composition may further comprise one or more crosslinking agents.

Crosslinking agents may be used to increase the strength and abrasion resistance of the coating. Crosslinking agents may also promote adhesion of the coating composition to the substrate.

Non-limiting examples of suitable crosslinking agents include 3-glycidyloxypropyl trimethoxysilane, 3-(trimethoxysilyl)propyl methacrylate, 3-(trimethoxysilyl)propyl acrylate, vinyltrimethoxysilane, allyltrimethoxysilane, tetrakis(trimethylsilyloxy)silane, poly(ethylene glycol) diglycidyl ether, poly(ethylene glycol) diacrylate, poly(ethylene glycol) dimethacrylate, poly(ethylene glycol) divinyl ether, branched trialkyloxy silanes, branched epoxides, and branched acrylates and methacrylates.

Other examples of thermally activated, chemically activated, and UV-activated crosslinkers are generally known to those skilled in the art.

A preferred crosslinking agent is 3-glycidyloxypropyl trimethoxysilane (GOPS).

Without being bound to a particular theory, it is believed that the GOPS epoxide moieties can attach to neighboring epoxides and/or to the PSS backbone (if the conductive polymer comprises PEDOT:PSS), while the GOPS silane moieties can attach to neighboring silane moieties and/or to hydroxyl moieties present on the surface of a metal or polymer substrate.

Furthermore, because GOPS is a thermally activated crosslinker, it activates during the curing step and does not require the coating process to comprise an additional crosslinking activation step (e.g., a chemical or UV-initiated activation step).

Other epoxide- and silane-containing crosslinkers would be expected to exhibit properties similar to GOPS to the extent that they comprise the respective epxoxide and silane moieties.

In some cases, the precursor solution comprises one or more ionic additives that can provide an ionic bridge between functional groups present on the substrate and on the conducting polymer and/or primary counterion. The ionic additives may comprise, for example, metal ions. Preferably, the precursor solution comprises alkaline earth metal ions (e.g., $Ca^{2+}$).

The crosslinking agent is typically included in a concentration of from about 0.1% to about 10% of the precursor composition on a weight per volume basis. More typically, the concentration of the surfactant component is from about 0.1% to about 5% w/v, and more typically from about 0.5% to about 4% w/v.

Flexibility Enhancers

The coating precursor solution may comprise one or more flexibility enhancers.

The compositions described herein may be applied as conformal coatings on three-dimensional substrates having a high degree of flexibility (e.g., flexible tubing). It is therefore desirable for the coatings described herein to resist physical deterioration (e.g., cracking) and continue to provide conductivity even after they are subjected to repeated flexing cycles.

To improve the flexibility of the coatings and achieve the properties listed above, one or more water-soluble, hydrophilic polymers may be added to the coating precursor composition.

Non-limiting examples of flexibility enhancers include polyacrylic acid, poly(acrylamide-co-acrylic acid), polyvinylpyrrolidone, polyvinyl alcohol, poloxypropylene-polyoxyethylene polaxamers (e.g., PLURONIC F-68, PLURONIC F-127), poly(2-acrylamido-2-methyl-1-propanesulfonic acid), sulfonated polytetrafluoroethylene (e.g., NAFION), polystyrene sulfonic acid, polystyrene sulfonate, poly(acrylic acid-co-maleic acid), poly(2-hydroxyethyl methacrylate), polyanetholsulfonic acid sodium salt, polyvinyl sulfonic acid sodium salt, poly(1-vinylpyrrolidone-co-vinyl acetate), polystyrene-block-poly(ethylene-r-butylene)-block-polystyrene sulfonate, polyethylene glycol, polyethylene oxide, or a combination thereof.

Preferred flexibility enhancers include poly(acrylamide-co-acrylic acid), polyvinyl pyrrolidone, polyvinyl alcohol, polyethylene glycol, polyethylene oxide, or a combination thereof. Polyvinyl pyrrolidone is a particularly preferred flexibility enhancer.

Alternatively, the precursor solution may comprise monomer forms of any of the water-soluble, hydrophilic polymer species listed above. The monomer can be polymerized into the corresponding polymer species through incorporation of a radical initiator. A non-limiting example of a preferred radical initiator is sodium persulfate.

The coatings described herein typically maintain their conductivity following repeated flexing cycles to a greater degree than compositions known in the prior art. For example, the coatings typically exhibit an increase in electrical resistance of no more than 50%, no more than 40%, no more than 30%, no more than 20%, or no more than 10% as measured according to the flexibility test set forth in Example 5.

The flexibility enhancer is typically included in a concentration of from about 0.005% to about 5% of the precursor composition on a weight per volume basis. More typically, the concentration of the flexibility enhancer is from about 0.1% to about 1% w/v, and more typically from about 0.1% to about 0.5% w/v.

Thickening Agents

The coating precursor composition may comprise one or more thickening agents to increase the viscosity of the composition, thereby reducing the total number dips required to achieve a desired coating thickness. In general, thicker coatings are desirable they exhibit a lower electrical resistance.

The thickening agent may also be used to improve the adhesion, cross-linking, flexibility, lubricity, and/or abrasion resistance of the coating.

Non-limiting examples of suitable thickening agents include polyacrylic acid, poly(acrylamide-co-acrylic acid), polyvinylpyrrolidone, polyvinyl alcohol, poly(2-acrylamido-2-methyl-1-propanesulfonic acid), sulfonated polytetrafluoroethylene (e.g., NAFION), polystyrene sulfonic acid, polystyrene sulfonate, poly(acrylic acid-co-maleic acid), poly(2-hydroxyethyl methacrylate), polyanetholesulfonic acid sodium salt, polyvinyl sulfonic acid sodium salt, poly(1-vinylpyrrolidone-co-vinyl acetate), polystyrene-block-poly(ethylene-r-butylene)-block-polystyrene sulfonate, polyethylene glycol, polyethylene oxide, poloxypropylene-polyoxyethylene polaxamer (e.g., PLURONIC F-68, PLURONIC F-127), or a combination thereof.

Preferred thickening agents include polyacrylic acid, polyethylene glycol, and polyacrylamide. Polyacrylic acid is a particularly preferred thickening agent.

The thickening agent is typically included in a concentration of from about 0.001% to about 1% of the precursor composition on a weight per volume basis. More typically, the concentration of the thickening agent is from about 0.01% to about 0.5% w/v, and more typically from about 0.01% to about 0.2% w/v.

Conductive Fillers

The coating precursor solution may comprise one or more additional conductive materials, sometimes referred to herein as conductive fillers, that reduce the contact resistance of the coating composition. Preferably, the additional conductive materials also improve the bulk conductivity of the coating composition.

The additional conductive materials may provide additional properties to the coating composition, such as radiopacity, imaging contrast, EM absorption, energy generation, and/or energy storage.

Non-limiting examples of additional conductive materials include metal particles, metal shavings, metal fibers, conductive carbon, carbon black, carbon fiber, graphite, graphene, carbon nanotubes, carbon fiber silicon, silicon particles, quaternary ammonium salts and ions, polyelectrolytes, ionomers, and other salts and ionic compounds known in the art.

For example, the additional conductive materials may comprise carbon fiber, carbon nanotubes (e.g., multi-walled carbon nanotubes), stainless steel flakes (e.g., 316L stainless steel), nickel flakes, stainless steel nanopowder, graphite, graphene, or noble metals (e.g., high conductivity spheres).

Preferred conductive materials include microfine graphite and multiwall carbon nanotubes.

Typically, the additional conductive materials are added to the coating precursor composition in the least amount that is sufficient to reduce the contact resistance associated with the use of a conductive polymer (e.g., PEDOT).

For example, the additional conductive materials are typically added in a concentration of no more than about 25%, no more than about 20%, no more than about 15%, no more than about 10%, or no more than about 5% of the coating precursor composition on a weight per volume basis.

The conductive materials may be added to the coating precursor composition in a concentration of from about 1% to about 20% on a weight per volume basis, from about 1% to about 10% on a weight per volume basis, from about 2% to about 10% on a weight per volume basis, from about 1% to about 5% on a weight per volume basis, or from about 2% to about 5% on a weight per volume basis.

Monomer Additives

The coating precursor composition may further comprise one or more monomer additives to enhance the adhesion, cohesion, abrasion resistance, lubricity, and/or flexibility of the coating composition.

For example, the precursor composition may comprise one or more methacrylate, acrylate, and/or acrylamide based monomers. Non-limiting examples include polyethyleneglycol dimethacrylate, 2-hydroxyethyl methacrylate, and 2-acrylamido-2-methylpropane sulfonic acid.

As a further example, the precursor composition may comprise one or more vinyl based monomers, such as styrene sulfonic acid.

The monomers may be polymerized by means known to those skilled in the art, including thermal initiated polymerization, UV-initiated polymerization, and/or radical-initiated polymerization.

Photo-active binders or photopolymers may be added to the precursor composition for patterning or stereolithographic printing of conductive components. Non-limiting examples include 4,4'-diazidostilbene-2,2'-disulfonic acid disodium salt, aryl azides, fluorinated aryl azides, benzophenones, and multifunctional derivatives thereof.

Stabilizers

The coating precursor composition may further comprise one or more stabilizers to protect the coating composition against chemical degradation, including degradation caused by free radicals, ultraviolet radiation, heat, and/or ozone exposure.

Non-limiting examples of suitable stabilizers include 2,2, 6,6-tetramethyl piperidine and its derivatives, benzophenones, benzofuranones, oxanilides, p-phenylenediamines, N-(1,3-dimethylbutyl)-N'-phenyl-p-phenylenediamine, N-isopropyl-N'-phenyl-p-phenylenediamine, 6-ethoxy-2,2, 4-trimethyl-1,2-dihydroquinoline, ethylene diurea, hindered phenols, aromatic amines, benzotriazoles, and hydroxyphenyltriazines.

Swelling Agents

The coating precursor composition may further comprise one or more swelling agents that promote incorporation of the conductive polymer coating into the substrate, rather than merely adhesion of the coating to the top of the substrate.

By limiting the duration of exposure to the swelling agent, any potential damage to the underlying substrate can be minimized.

Non-limiting examples of swelling agents include polar solvents such as acetonitrile, acetone, and dimethylformamide.

Biological Components

The coating precursor composition may further comprise one or more natural or synthetically-produced bioactive compounds that can translate biochemical changes into electrical signals, and which can be incorporated into the coating composition to create bio-sensor surfaces.

Non-limiting examples of suitable bioactive compounds include enzymes, DNA, and RNA segments.

Active Particles

The coating precursor composition may further comprise one or more electrically active particles.

For example, electrically active particles such as light-emitting or light-absorbing compounds can be immobilized in the conductive polymer coating to provide a composite material that provides energy/power generation, light emission, circuitry, or sensing capabilities.

Organic light-emitting diode, photovoltaic, and/or sensing particles may be incorporated into the precursor composition.

Methods of Coating Substrates

Another aspect of the present invention is directed to a method of applying conformal coatings to three-dimensional substrates.

Generally, the method comprises (1) preparing a coating precursor composition as described above, (2) applying the coating precursor to a substrate using a dip coating process, and (3) thermally curing the coated substrate. Steps (2) and (3) may be repeated as necessary until the desired coating thickness is achieved.

Substrates

The coatings described herein may be applied to a wide variety of substrate materials that are known in the art.

For example, the substrate can be electrically conductive or not electrically conductive.

The substrate may comprise a polymer. The coating compositions and methods described herein are compatible with an extremely large and diverse group of polymers.

Non-limiting examples of suitable polymeric substrates include PET, PE, PP, PU, TPU, poly(p-xylylene) (e.g., PARYLENE), SU-8, nylon, PGA, PLA, PGLA, PEBAX, polycarbonate, PMMA, acrylics, PVC, polyimide, rubber, latex, NBR, SIBS, silicone, photoresist, polyester, polystyrene, p(2-HEMA), and PEEK.

The substrate may comprise one or more composite materials, such as epoxy-reinforced fiberglass or carbon fiber.

By way of non-limiting example, the substrate can comprise a carbon nitride, a carbon cloth, a carbon paper, a carbon screen printed electrode, a carbon black, a carbon powder, a carbon fiber, a carbon nanotube, a diamond-coated conductor, a glassy carbon, a mesoporous carbon, a graphite, or a combination thereof.

The substrate can comprise a non-metallic inorganic material. For example, the non-metallic inorganic material can comprise a metal oxide, a metal nitride, a ceramic, a metalloid, or a combination thereof. More typically, the non-metallic inorganic material comprises a metalloid comprised of silicon, carbon, or a combination thereof.

The substrate can comprise a metal oxide. For example, the metal oxide can comprise aluminum, titanium, zirconium, hafnium, tantalum, molybdenum, tungsten, rhenium, iridium, or a combination thereof.

The substrate may comprise a ceramic. The coating compositions described herein can be applied onto insulating or semiconductive ceramics to provide electrical conductivity such as circuits, shielding, or electrostatic discharge. Ceramics that may be coated as described herein include but are not limited to silicone, silicon dioxide, glass, alumina, indium tin oxide, among others.

For example, the ceramic can comprise a silicon nitride, a silicon carbide, a silicon oxide, a calcium phosphate, or a combination thereof.

The substrate may comprise a metal. The coating compositions described herein provide a number of benefits when applied to metal substrates, including but not oimited to corrosion resistance, immobilization of electro-active or bioactive compounds on the metal surface, or to increase the conductivity or charge storage capabilities of the metal.

For example, the substrate can comprise a metal comprised of a noble metal, a transition metal, or a combination thereof. For example, the metal can be selected from the group consisting of gold, platinum, palladium, iridium, osmium, rhodium, titanium, tantalum, tungsten, ruthenium, magnesium, iron, or a combination thereof.

The substrate can comprise a non-noble metal. For example, the non-noble metal can be comprised of titanium, tantalum, or a combination thereof.

The substrate can comprise a metal alloy. Typically, the metal alloy comprises at least one noble metal and at least one transition metal. By way of non-limiting example, the metal alloy can comprise iron, sulfur, manganese, and molybdenum; iron and chromium; nickel and titanium; nickel and cobalt; cobalt and chromium; cobalt, chromium and iron; cobalt, chromium and nickel; cobalt, chromium, nickel and tungsten; nickel and chromium; magnesium and iron; or a combination thereof. For example, the metal alloy can comprise nickel and cobalt. The metal alloy can also be a stainless steel alloy comprised of stainless steel 304L, stainless steel 316L, stainless steel 316LVM, stainless steel MP35N, stainless steel 35NLT, or a combination thereof.

The substrate may comprise one or more biological and/or natural materials. For example, the coatings described herein can be applied to biological materials such as human or animal tissues, organs, cells, body parts, tissue scaffolds, nerves, and bones, as well as natural materials such as wood.

Generally, the substrates can have almost any form, including but not limited to metal pieces, coupons, meshes, foams, textiles, wires, blocks, tubes, and/or spheres.

The substrate can comprise all or part of one or more electrodes on a device, for example a medical device.

Preferably, the substrate comprises a foam.

The substrate can comprise a cylindrical tube.

Substrate Preparation

The process may optionally comprise one or more steps for preparation of the substrate prior to coating.

Prior to application of the coating, the conductive substrate should be as uniform as possible, and should be clean and free of organic material/molecules, dust and other contaminants so that the coating comes into direct and complete contact with the underlying substrate. Substrate cleaning can be achieved a number of ways with varying degrees of harshness, including but not limited to rinsing and/or ultrasonicating in water or soapy water, exposure to organic solvents such as acetone or alcohol, hydrogen peroxide, acids or etching solutions (e.g. Pirhana etch), exposure to reactive plasma cleaning/etching such as $O_2$ or $CF_4$, or microgrit blasting with media such as sodium bicarbonate, silica, and alumina. After cleaning, the conductive substrate is typically dried under a stream of nitrogen or argon to limit exposure to oxygen, which can contaminate the cleaned surface. It is sometimes preferable to store the cleaned substrates (prior to coating) in oxygen-free environments (e.g., a glove box purged with nitrogen).

The surface of the substrate can be modified with an organic molecule layer. Non-limiting examples of an organic molecule layer include an oxide layer, a monolayer, or self-assembled monolayer, or a tie layer. Organic molecule surface modification can be employed to modulate physical properties of the coated substrate including but not limited to coating adhesion, conductivity, and uniformity. Non-limiting examples of surface functional groups include thiols and silanes. Molecular modification of the surface of the substrate can be achieved in a number of ways, including but not limited to reactive plasma exposure, soaking/dip-coating or micro/nano spray with molecular solution, electrochemical mediated oxidation/reduction of a metal surface, and/or electro-grafting of molecular species For example, if the substrate is a polymer substrate, $O_2$ plasma treating can be used prior to the coating step to improve wettability and adhesion of the coating composition. $O_2$ plasma treating is particularly preferred where the substrate comprises a poly(p-xylylene) polymer (e.g., PARYLENE).

Dip-Coating Step

The coating precursor composition is typically applied to the substrate using a dip coating process.

Typically, the substrate is fully submerged in a bath comprising the coating precursor solution. More generally, the substrate should be submerged in a manner that allows the coating precursor solution to reach all areas of the substrate surface where a coating is desired.

A dip coater can be used to control the rate at which the substrate is immersed and removed from the coating solution. Typically, the use of a dip coater results in a more uniform coating. Typical dip coating rates are from about 1 to about 5 mm/s, and more typically from about 2 to about 3 mm/s.

If necessary, multiple dips may be utilized to achieve the desired final coating thickness. For example, the final coating may have a thickness of at least about 0.5 microns, at least about 1 micron, at least about 2 microns, at least about 3 microns, at least about 4 microns, or at least about 5 microns.

Typically, the substrate is coated with a conductive coating having a thickness of from about 200 nm to about 10 µm. More typically, the substrate is coated with a conductive coating having a thickness of from about 500 nm to about 5 µm.

Following each dip, the substrate is baked at a short time to set the most recently applied layer of the coating. Typically, the substrate is typically baked for from about 2 minutes to about 30 minutes between coatings at a temperature of from about 80° C. to about 160° C.

More typically, the substrate is baked following each dip for from about 2 minutes to about 20 minutes, from about 3 minutes to about 15 minutes, from about 3 minutes to about 10 minutes, or from about 3 minutes to about 7 minutes.

More typically, the substrate is baked following each dip at a temperature of from about 100° C. to about 150° C., from about 120° C. to about 145° C., from about 125° C. to about 140° C., or from about 130° C. to about 140° C.

The short baking step is not necessary following application of the final coat. Instead, the coated substrate is subjected to a thermal curing step as described below.

Thermal Curing Step

After the final dip, when the desired coating thickness has been achieved, the coated substrate is thermally cured.

The thermal curing step involves baking the substrate at an increased temperature for a significantly longer period than the relatively short baking periods following each dip.

For example, the thermal curing step typically involves baking the substrate for from about 15 minutes to about 4 hours at a temperature of from about 80° C. to about 160° C.

More typically, the substrate is baked for from about 20 minutes to about 3 hours, from about 30 minutes to about 2.5 hours, from about 45 minutes to about 2 hours, or from about 45 minutes to about 1.5 hours.

More typically, the substrate is baked at a temperature of from about 100° C. to about 150° C., from about 120° C. to about 145° C., from about 125° C. to about 140° C., or from about 130° C. to about 140° C.

Those skilled in the art will appreciate that certain substrates may require the thermal curing step to be carried out at a lower temperature and for a longer period of time.

Generally, the thermal curing step should be conducted at a temperature that is low enough to maintain the integrity of the substrate material, and for a sufficient period of time to affect complete or substantially complete removal of the solvent component from the coating.

UV Polymerization Step

When the coating precursor solution comprises one or more monomers that can be polymerized using UV-initiated polymerization, the process may further comprise a UV-initiated polymerization step.

Generally, the UV-initiated polymerization step can be carried out by one of ordinary skill in the art using known methods. The UV-initiated polymerization step can be performed before, after, or simultaneously with the thermal curing step.

Coated Substrates

In a further aspect, the present invention is directed to coated substrates produced in accordance with the methods described herein.

Generally, the substrate may be selected as described in detail above. The coating may be prepared according to the methods described herein, and/or derived from a coating precursor composition as described herein.

Cylindrical Tube Electrode

For example, the coated substrate may comprise a cylindrical tube electrode comprising an inner lumen and an outer surface, wherein a polymeric coating comprising one or more conductive layers is adhered to the outer surface. One or more of the conductive layers may comprise a conductive coating composition prepared according to the methods described herein, and/or derived from a coating precursor composition as described herein.

The coating composition can further comprise one or more insulating layers. For example, the coating composition may comprise alternating conductive and insulating layers.

Conductive Foams and Textiles

In another aspect, the coated substrate may comprise an electrically conductive composite material having a high surface area. For example, the coated substrate may comprise an electrically conductive foam.

The foam may be, for example, a polyurethane foam. As a further example, the coated substrate may comprise an electrically conductive textile.

Coated Electrodes

In another aspect, the coated substrate may comprise a coated electrode comprising an electrically conductive substrate and a polymeric coating, wherein a polymeric coating comprising one or more conductive layers is adhered to the outer surface. One or more of the conductive layers may comprise a conductive coating composition prepared according to the methods described herein, and/or derived from a coating precursor composition as described herein.

Non-limiting examples of coated electrodes include needle electrodes and ring electrodes.

Polymer Electrodes

The compositions and methods described herein can also be used to prepare all-polymer electrodes having no metal or ceramic substrate.

Medical Devices

Another aspect of the present invention is directed to a medical device comprising a coated substrate as described above. For example, the medical device can be an implantable medical device.

Having described the invention in detail, it will be apparent that modifications and variations are possible without departing from the scope of the invention defined in the appended claims.

EXAMPLES

The following non-limiting examples are provided to further illustrate the present invention.

Example 1: Electrically Conductive Coating on Foam

Prepare a coating solution with 80:20 volume ratio of Clevios PH 1000 PEDOT:PSS dispersion and ethylene glycol, respectively. Add 3-glycidyloxypropyl trimethoxysilane at 1% w/v and dodecylbenzenesulfonic acid at 0.2% w/v. Stir components until thoroughly mixed, or for at least 30 minutes.

Fully submerge the foam in the coating solution. Remove foam from coating solution and allow excess coating solution to run off. It is also possible to use rollers to squeeze excess coating solution out of the foam. Use compressed air or nitrogen to blow excess coating solution off of the foam and give a uniform coating across the entire foam surface.

Cure the coating by baking for 60 minutes at 135° C. If multiple coatings are required to increase conductance of the coated foam, it is acceptable to bake 5-20 minutes between coatings and 60 minutes after the final coating.

Example 2: Electrically Conductive Coating on Polyurethane Tubing with Enhanced Flexibility Prepare a coating solution with 80:20 volume ratio of Clevios PH 1000 PEDOT:PSS dispersion and ethylene glycol, respectively. Add 3-glycidyloxypropyl trimethoxysilane at 1% w/v, dodecylbenzenesulfonic acid at 0.2% w/v, and poly(acrylamide-co-acrylic acid) (20% acrylic acid by monomer, Mw 520,000) at 0.2% w/v. Stir components until thoroughly mixed, or at least for two hours.

Cut 30 cm lengths of Superthane ether-based 0.25 inch outer-diameter, 0.125 inch inner-diameter polyurethane tubing. Straighten polyurethane tubing for dip coating by running 22 gauge stainless steel rod the entire length of the polyurethane tube lumen. Close the bottom end of the polyurethane tubing with shrink tube to prevent coating solution from entering the lumen. Clean polyurethane tubes with laboratory soap and water immediately prior to dip coating.

Dip coat at 3 mm/s constant rate. Cure coating at 135° C. for 60 minutes. If multiple coatings are required to increase conductance of the coated polyurethane tube it is acceptable to bake 5 minutes between dip coats and 60 minutes after the final coating.

Example 3: Electrically Conductive Coating on Polyurethane Tubing with Enhanced Flexibility Alternative Prepare a coating solution with 95:5 volume ratio of Clevios PH 1000 PEDOT:PSS dispersion and ethylene glycol, respectively. Add 2-Acrylamido-2-methylpropane sulfonic acid monomer at 2% w/v, poly(ethylene glycol) dimethacrylate (Mn 750) at 0.2% w/v, sodium persulfate at 0.1% w/v, and dodecylbenzenesulfonic acid at 0.2% w/v. Stir components until thoroughly mixed, or at least for 30 minutes.

Cut 30 cm lengths of Superthane ether-based 0.25 inch outer-diameter, 0.125 inch inner-diameter polyurethane tubing. Straighten polyurethane tubing for dip coating by running 22 gauge stainless steel rod the entire length of the polyurethane tube lumen. Close the bottom end of the polyurethane tubing with shrink tube to prevent coating solution from entering the lumen. Clean polyurethane tubes with laboratory soap and water immediately prior to dip coating.

Dip coat at 3 mm/s constant rate. Cure coating at 135° C. for 60 minutes. If multiple coatings are required to increase conductance of the coated polyurethane tube it is acceptable to bake 5 minutes between dip coats and 60 minutes after the final coating.

Example 4: Electrically Conductive Coating on Parylene C Coated Needles with Decreased Contact Resistance Prepare a coating solution with 95:5 volume ratio of Clevios PH 1000 PEDOT:PSS dispersion and ethylene glycol, respectively. Add 3-glycidyloxypropyl trimethoxysilane at 5% w/v, dodecylbenzenesulfonic acid at 0.5% w/v, and Southwestern Graphite Microfyne graphite powder at 5% w/v. Stir components until thoroughly mixed, or at least for two hours.

Parylene C coated 22 gauge needles are treated with oxygen plasma prior to dip process to provide a substrate for dip coating that enhances uniformity and adhesion. If necessary, mask areas of the needles not to be coated with coating solution using polyimide tape or PTFE tape. Use shrink tube to close the lumen on the bottom of the needles to prevent coating solution from entering the lumen. Clean the Parylene C coated needles with laboratory soap and water immediately prior to dip coating.

Dip coat at 2 mm/s constant rate. Cure coating at 135° C. for 60 minutes. If multiple coatings are required to increase conductance of the coated needle it is acceptable to bake 5 minutes between dip coats and 60 minutes after the final coating.

Example 5: Flexibility Performance of Coated Cylindrical Tubing

Four inch sections of polyurethane 0.25 inch OD tubes were dip coated (6 dips each) with a precursor composition as described in Example 1, and further comprising either no flexibility enhancer (Coating 1) or a flexibility enhancing compound (Coatings 2-4).

Changes in the resistance of each coating after flexing was measured by bending each tube around a 1.25 inch diameter rod 600 times. The first 300 flex cycles (#1-300) were performed by bending the sample the same direction. The second 300 flex cycles (#301-600) were performed by bending the sample in the opposite direction.

Resistance was measured across the coated tubes (using Ag contacts) before flexing (0 flexes) and every 100 flexes up to 600 total. The results of these measurements are shown below in Table 1.

TABLE 1

Electrical resistance of coated tubing samples after repeated flexing cycles

| | Coating 1 | Coating 2 | Coating 3 | Coating 4 |
|---|---|---|---|---|
| | No Flexibility Enhancer | 0.2% PEG | 0.2% PVP | 0.2% Pam-co-PAA |
| Flex Cycles | Resistance in Ohms | | | |
| 0 | 113 | 88 | 83 | 118 |
| 100 | 116 | 90 | 85 | 120 |
| 200 | 118 | 90 | 85 | 120 |
| 300 | 119 | 90 | 86 | 121 |
| 400 | 142 | 94 | 94 | 132 |
| 500 | 160 | 95 | 100 | 143 |
| 600 | 195 | 95 | 102 | 153 |
| % Change | 72.6% | 8.0% | 22.9% | 29.7% |

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there can be additional elements other than the listed elements.

In view of the above, it will be seen that the several objects of the invention are achieved and other advantageous results attained.

As various changes could be made in the above products and methods without departing from the scope of the invention, it is intended that all matter contained in the above description and shown in the accompanying drawings shall be interpreted as illustrative and not in a limiting sense.

What is claimed is:

1. An electrically conductive polymeric coating on a substrate, wherein the electrically conductive coating is derived from a coating precursor composition comprising:
   a conductive polymer component comprising poly(3,4-ethylenedioxythiophene) and a primary counterion comprising repeat units, wherein one or more of the repeat units have a negatively charged functional group;
   a secondary doping agent;
   a crosslinking agent comprising 3-glycidyloxypropyl trimethoxysilane;
   a surfactant component; and
   a flexibility enhancer comprising poly(acrylamide-co-acrylic acid), polyvinylpyrrolidone, polyvinyl alcohol, polyethylene glycol, polyethylene oxide, or a combination thereof.

2. The coating of claim 1 wherein the electrical resistance of the coating increases by no greater than 50% after 600 flexing cycles when the coating is applied to a substrate having an outer diameter of 0.25 inches and each cycle comprises flexing the coated substrate about a bend radius of 1.25 inches.

3. The coating of claim 1 further comprising a conductive filler comprising metal particles, carbon black, carbon fiber, graphite, graphene, carbon nanotubes, carbon fiber silicon, silicon particles, or a combination thereof, wherein the conductive filler is present in the electrically conductive polymeric coating in an amount sufficient to reduce the contact resistance of the polymeric coating, and wherein the conductive filler is present in the coating precursor composition in a concentration of no more than about 25% of the composition on a weight per volume basis.

4. The coating of claim 1 wherein the primary counterion comprises a negatively charged functional group comprising a phosphate group, a phosphonate group, a sulfamate group, a carboxylate group, a sulfate group, a sulfonate group, or a combination thereof.

5. The coating of claim 1 wherein the primary counterion comprises polyvinyl sulfonate, polystyrene sulfonate, polyallyl sulfonate, polyethyl acrylate sulfonate, polybutyl acrylate sulfonate, polyacryl sulfonate, polymethacryl sulfonate, poly-2-acrylamide-2-methylpropane sulfonate, polyisoprene sulfonate, polyvinyl carboxylate, polystyrene carboxylate, polyallyl carboxylate, polyacryl carboxylate, polymethacryl carboxylate, poly-2-acrylamide-2-methylpropane carboxylate, polyisoprene carboxylate, polyacrylates, polyglutamates, polydopamines, sulfonated poly ether ether ketones (S-PEEK), sulfonated polyurethanes, or a combination thereof.

6. The coating of claim 5 wherein the primary counterion comprises polystyrene sulfonate.

7. The coating of claim 1 wherein the coating precursor composition comprises poly(3,4-ethylenedioxythiophene):polystyrene sulfonate in the form of aqueous dispersion.

8. The coating of claim 1 wherein the coating precursor composition further comprises an organic solvent.

9. The coating of claim 1 wherein the secondary doping agent comprises a low volatility polar solvent selected from the group consisting of ethylene glycol, sorbitol, glycerol, dimethylsulfoxide, N,N-dimethylformamide, erythritol, 2-nitroethanol, methoxyphenol, N,N-dimethylacetamide, N-methylpyrrolidone, succinimide, propylene glycol, and combinations thereof.

10. The coating of claim 1 wherein the surfactant component comprises one or more anionic surfactants selected from the group consisting of alkylbenzenesulfonic acids and salts thereof, organosulfates, carboxylates, and natural fatty acids and salts thereof.

11. The coating of claim 10 wherein the surfactant component comprises dodecylbenzenesulfonic acid or sodium dodecyl sulfate.

12. The coating of claim 1 wherein the coating precursor composition further comprises a monomer additive comprising one or more methacrylate, acrylate, acrylamide, or vinyl based monomers.

13. The coating of claim 1 wherein the coating precursor composition further comprises a stabilizer selected from the group consisting of 2,2,6,6-tetramethyl piperidine and its derivatives, benzophenones, benzofuranones, oxanilides, p-phenylenediamines, N-(1,3-dimethylbutyl)-N'-phenyl-p-phenylenediamine, N-isopropyl-N'-phenyl-p-phenylenediamine, 6-ethoxy-2,2,4-trimethyl-1,2-dihydroquinoline, ethylene diurea, hindered phenols, aromatic amines, benzotriazoles, hydroxyphenyltriazines, and combinations thereof.

14. The coating of claim 1 wherein the coating precursor composition further comprises a swelling agent, and wherein the swelling agent comprises a polar solvent.

15. The coating of claim 1 wherein the coating precursor composition comprises: the crosslinking component in a concentration of from 0.1% to 10% of the precursor composition on a weight per volume basis; the secondary doping agent in a concentration of from 1% to 40% of the precursor composition on a weight per volume basis; and the surfactant component in a concentration of from 0.01% to 5% of the precursor composition on a weight per volume basis.

16. A cylindrical tube electrode comprising:
a cylindrical tube comprising an inner lumen and an outer surface,
and an electrically conductive polymeric coating adhered to the outer surface,
wherein the electrically conductive polymeric coating comprises one or more conductive layers, and
wherein one or more of said conductive layers comprises the electrically conductive polymeric coating of claim 1.

* * * * *